United States Patent
Chu et al.

(10) Patent No.: US 6,532,390 B1
(45) Date of Patent: Mar. 11, 2003

(54) INTRAMUSCULAR STIMULATION APPARATUS AND METHOD

(76) Inventors: Jennifer Chu, 2 Barrister Ct., Haverford, PA (US) 19041; Peter Styles, Brookwell, Bramley Guildford, Surrey GU5 0LQ (GB); Martin Nichols, Oxford Instruments Medical Ltd., Manor Way, Old Woking, Surrey GU22 9JU (GB); Robert Hopkins, Oxford Instruments Medical Ltd., Manor Way, Old Woking, Surrey GU22 9JU (GB)

( * ) Notice: Subject to any disclaimer, the term of this patent is extended or adjusted under 35 U.S.C. 154(b) by 0 days.

(21) Appl. No.: 09/702,772

(22) Filed: Nov. 1, 2000

(Under 37 CFR 1.47)

(30) Foreign Application Priority Data

Aug. 31, 2000 (GB) .............................................. 0021431

(51) Int. Cl.[7] .............................................. A61B 17/34
(52) U.S. Cl. ......................... 607/116; 607/48; 606/189; 128/907
(58) Field of Search ........................... 606/189; 607/48, 607/116; 128/907

(56) References Cited

U.S. PATENT DOCUMENTS

| | | |
|---|---|---|
| 4,180,079 A | 12/1979 | Wing |
| 4,276,879 A | 7/1981 | Yiournas |
| 4,613,328 A | 9/1986 | Boyd |
| 4,662,363 A | 5/1987 | Romano et al. |
| 4,758,227 A | 7/1988 | Lancaster, Jr. et al. |
| 5,199,952 A | 4/1993 | Marshall, Sr. et al. |
| 5,211,175 A | 5/1993 | Gleason et al. |
| 5,535,746 A | 7/1996 | Hoover et al. |
| 5,735,868 A | 4/1998 | Lee |
| 5,968,063 A | 10/1999 | Chu et al. |
| 5,976,167 A * | 11/1999 | Lee .............................. 606/189 |
| 6,058,938 A | 5/2000 | Chu et al. |
| 6,175,764 B1 | 1/2001 | Loeb et al. |
| 6,181,965 B1 | 1/2001 | Loeb et al. |

OTHER PUBLICATIONS

Jennifer Chu, M.D., "Dry Needling (Intramuscular Stimulation) in Myofascial Pain Related to Lumbosacral Radiculopthy", 1995, Eur. J. Phys. Med. Rehabil. 1995:5 No. 4, pp. 106–120.

Jennifer Chu, M.D., Comment on the Simons Literature Review Column, 'Myofascial Pain Syndrome—Trigger Points', J. Musculoskeletal Pain, vol. 5(1) 1997, pp. 133–135.

Photographs of IMS device purchased from Mr. Young H. Lee in Feb., 1996.

(List continued on next page.)

Primary Examiner—Michael Powell Buiz
Assistant Examiner—Ramesh Krishnamurthy
(74) Attorney, Agent, or Firm—Banner & Witcoff, Ltd.

(57) ABSTRACT

An intramuscular stimulation (IMS) device and method permit electrical and mechanical modes of stimulation to be carried out individually or together. The gun-like stimulation device permits a disposable needle applicator unit including a needle and elongate sheath to be removably attached thereto. Different needle penetration depths are obtainable with a single needle by virtue of a drive carriage with a position selecting element. To help avoid repetitive strain injury to a treating physician, a processor may monitor a body contact sensor and continue an intramuscular stimulation cycle only so long as contact is detected. In order to ensure that only a single IMS operation is performed during a period of body contact, performance of a further intramuscular stimulation cycle may be prevented unless it is determined that body contact was broken at a time following a previous IMS cycle.

33 Claims, 5 Drawing Sheets

OTHER PUBLICATIONS

C. C. Gunn, et al., "Dry Needling of Muscle Motor Points for Chronic Low–Back Pain: A Randomized Clinical Trial With Long–Term Follow–Up", Spine, vol. 5, No. 3, May/Jun. 1980, pp. 279–291.

C. Chan Gunn, M.D., "Treating Myofascial Pain: Intramuscular Stimulation (IMS) for Myofascial Pain Syndromes of Neuropathic Origin", 1989.

C. Chan Gunn, M.D., "The Gunn Approach to the Treatment of Chronic Pain: Intramuscular Stimulation for Myofascial Pain of Radiculopathic Origin", (2d ed.), 1996.

Open letter re IMS treatment offered by Jennifer Chu, M.D., University of Pennsylvania Medical Center, Mar. 13, 1996.

"Patient Information on Intramuscular Stimulation (IMS) For Management of Soft–Tissue/Neuropathic Pain", University of Pennsylvania Medical Center, Apr. 8, 1996.

Travell, J.G., Simons, D.G., "Myofascial Pain and Dysfunction: The Trigger Point Manual," vol. 1. Wiliams and Wilkins, Baltimore, 1983, Table of Contents, Preface, Chapter 3 "Apropos of Muscles."

Travell, J.G., Simons, D.G., "Myofascial Pain and Dysfunction: The Trigger Point Manual," vol. 2. The Lower Extremities. Wiliams and Wilkins, Baltimore, 1992, Table of Contents, Chapter 2 "General Issues."

The NeuroControl StIM™ System Clinician Manual, Doc. # 265–1005–P, Neuro Control Corp., 1999–2000.

* cited by examiner

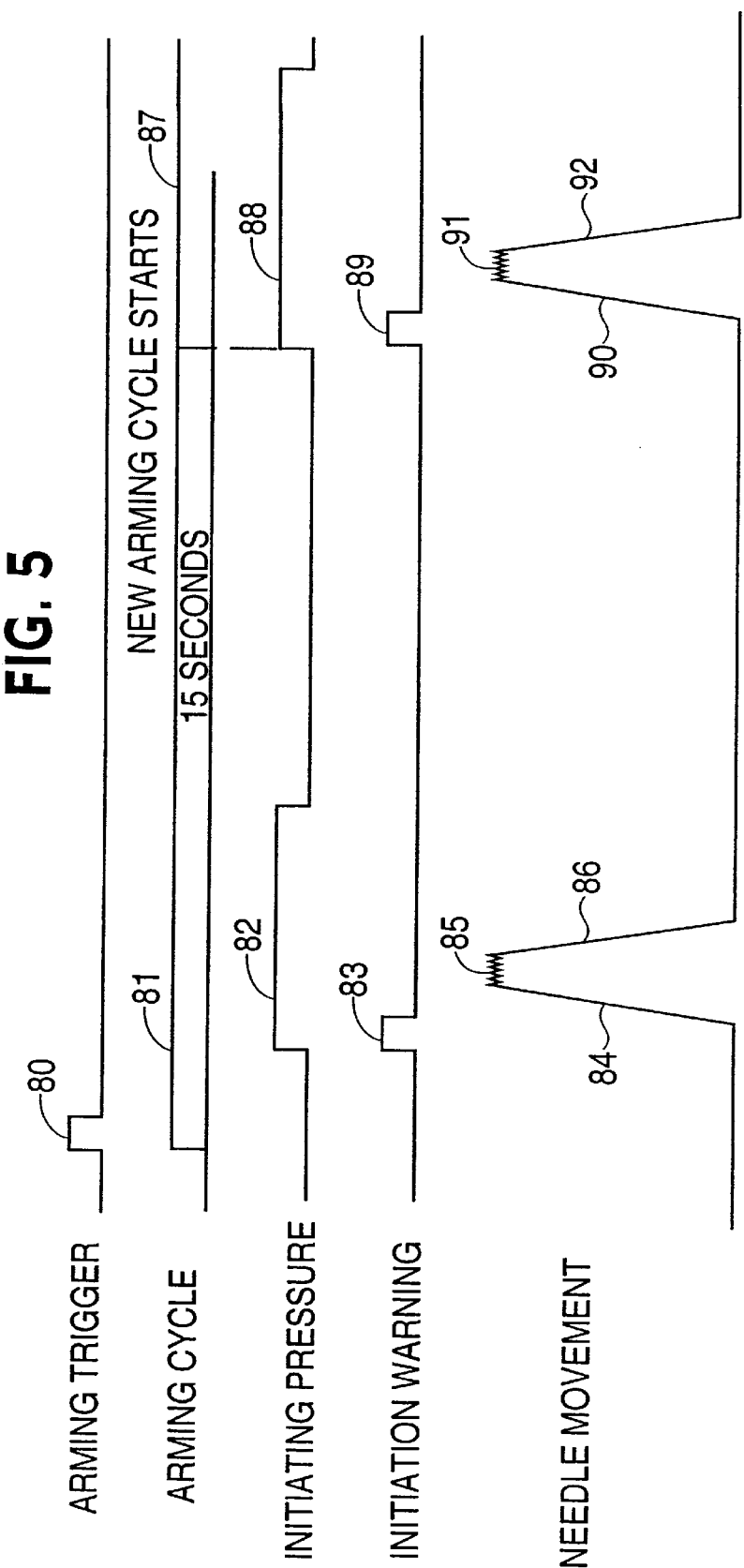

INTRAMUSCULAR STIMULATION APPARATUS AND METHOD

BACKGROUND OF THE INVENTION

The present invention relates to a method and apparatus for performing intramuscular stimulation.

It has been determined by a number of workers that severe chronic musculoskeletal pain caused by muscles shortening within the body, can be relieved by a technique similar to acupuncture. However, unlike in acupuncture, this method known generally as "intramuscular stimulation" (IMS), involves the insertion of a needle into a region where the nerves connect with the muscle, the motor point region, where the muscle may be readily stimulated or "twitched".

The stimulation of the muscle is effected by either mechanical manipulation, electrical stimulation or a combination of both.

In many cases the technique necessitates multiple needle insertions into the body of a patient and often at many sites in an affected region. Conventionally, IMS has been performed manually by a physician. This manual technique is very tiring for the physician and has even been known to cause repetitive strain injury. This is because conventional manual stimulation of the muscles is achieved by inserting the needle to the motor point where the muscle may be stimulated so as to cause the muscle to twitch.

Manual stimulation generally involves a reciprocal motion of the needle for a number of seconds. The muscle then relaxes after removal of the needle.

A second method of stimulation is to pass an electric current into the motor point region which causes similar stimulation of the muscle. This can be advantageous as the electric current may stimulate a number of muscles in the area surrounding the needle. Alternatively a combination of manual and electrical IMS has also been found to be effective.

An example of the automation of this method is disclosed in U.S. Pat. No. 5,968,063 and U.S. Pat. No. 6,058,938. In this case one end of a conventional acupuncture or electromyography (EMG) needle is attached to a coupling device which in turn is coupled to the drive mechanism of a gun. In use, the gun is placed against the skin and the second end of the needle is driven from the end of the gun through a nozzle touching the skin and into the patient.

Although the use of automatic devices represents a significant advance upon manual manipulation, there are a number of problems associated with them.

Conventional EMG and acupuncture needles are available in a number of different sizes according to the depth of penetration which should be used. Some problems are encountered in attaching these various different size needles to the coupling device of the gun whilst maintaining the integrity and sterility of the needles. In addition, if the subject requires treatment of different muscular groups within the body, the use of different needles having different lengths is therefore required, necessitating a change of needles between the treatments of different muscle groups.

SUMMARY OF THE INVENTION

In accordance with a first aspect of the present invention, we provide a disposable needle applicator unit for attachment to an intramuscular stimulation device, the applicator unit comprising:

a needle having an elongate first end portion for insertion into the body of a subject and a second end portion for coupling with a drive carriage of the intramuscular stimulation device; and an elongate sheath for enclosing at least the first end portion of the needle, the sheath having a first opening in one end from which the first end portion of the needle may be extended, and a second opening allowing the second end portion of the needle to be coupled with the drive carriage.

The use of a disposable needle applicator unit provides many advantages, particularly in that the sterility of the needle may be more readily assured. The needle applicator unit may be conveniently coupled directly to the drive carriage of the intramuscular stimulation device whilst the sheath provides protection of the portion of the needle that is to be inserted into the body.

As the needle is contained safely within the sheath when the applicator unit is being fitted or attached to the device, the risk of cross-contamination between the patient and physician due to accidental penetration of the physician's skin with the needle, is significantly reduced. The unit therefore provides a further advantage in that, following use, it can be detached from the IMS device and disposed of in its entirety.

Typically the first opening of the sheath will be arranged to tightly enclose the needle so as to precisely guide the first end portion of the needle into the subject in a rectilinear manner with a minimum amount of needle distortion, which is known to cause discomfort in the subject.

Although the second opening of the sheath may be arranged in a number of locations allowing access to the needle, preferably it will take the form of a slot arranged in the side of the sheath such that the second end portion of the needle may be coupled to the drive carriage of the IMS device.

The drive carriage may be arranged such that a coupling element passes through the opening of the sheath to couple with the needle. However, in general the second end portion of the needle will be arranged to project through the second opening of the sheath in order to couple externally to the drive carriage. This may be achieved for example by arranging the second end portion of the needle to be at an angle with respect to the first end portion, for example projecting through the second opening slot.

The first end portion of the needle may then move in the first direction through the first opening of the sheath, as the second end portion moves along the slot whilst projecting from it. In this way a single needle may be used for performing an IMS cycle at different penetration depths upon different muscle groups.

Typically at least the first end portion of the needle will be coated in a friction reducing layer such as PTFE. However, the coating may be removed at the extreme tip of the first end portion where the needle may be sharpened. This allows the tip of the needle to make a good electrical contact with the motor point of the subject.

The needle may be formed as a single component. Preferably however the needle will comprise two or more components. Typically therefore the needle may comprise first and second elongate components arranged axially end to end and coupled such that the first end portion is formed from part of the first component and the second end portion is formed from the second component. The second elongate component may be arranged with an internal bore within which part of the first elongate component may be received.

The two components of the needle may be releasably coupled but preferably they will be coupled in a non-releasable manner. This may be achieved for example with metallic components by crimping them together.

The IMS device may be arranged to have a gripping mechanism to which the applicator unit may be attached. However, preferably the applicator unit will further comprise an attachment element to allow attachment to the IMS device, the attachment element typically comprising one or more projections for coupling with one or more corresponding elements on the intramuscular stimulation device.

Preferably, the applicator unit will also further comprise a contact block arranged at the rear of the sheath with respect to the first opening, wherein in use, the contact block couples with a corresponding component of the intramuscular stimulation device such that the applicator unit is securely attached to it. For example, a plunger attached to the intramuscular stimulation device may apply a force to the block so as to urge the applicator unit in the first direction.

Typically the applicator unit will further comprise a detent arranged to releasably retain the needle such that the first end portion of the needle is enclosed within the sheath when the applicator unit is not attached to the intramuscular stimulation device.

Preferably the applicator unit according to the first aspect of the present invention will be used in conjunction with a corresponding IMS device.

The use of automatic devices raises safety issues in that the accurate control of the penetration and stimulation cycles should be provided with safeguards such that the patient will not become injured in the event of a device malfunction.

In accordance with a second aspect of the present invention, we provide an intramuscular stimulation device comprising:
  a drive carriage to which a needle is coupled in use, the drive carriage being arranged so as to move the needle in a first direction to one of a number of predetermined positions for subsequently performing intramuscular stimulation of a subject;
  a drive motor arranged to operate the drive carriage;
  a position selecting element arranged to produce a signal identifying the selection of a particular predetermined position from the number of predetermined positions, the signal being used in accordance with the drive motor and drive carriage to move the needle in the first direction to the selected predetermined position; and,
  a stop which can be located in accordance with the selected predetermined position so as to prevent the needle from moving past the selected predetermined position.

The IMS device of the second aspect of the invention will be typically used in association with the disposable needle applicator unit according to the first aspect of the present invention.

The selection of predetermined needle positions has associated safety problems and therefore the stop provides a physical safeguard to the further movement of the needle beyond the predetermined position.

Preferably, the drive carriage will be coupled to the needle by the insertion of a portion of the needle in a corresponding hole arranged in the drive carriage. This is particularly convenient when the device is used in conjunction with the needle applicator unit having a second end portion of the needle projecting from the applicator unit sheath.

The drive carriage is typically arranged to be driven to and fro in the first direction by a motor and it may not only provide the motion required for moving the needle to one of the predetermined positions, but also any subsequent reciprocal motion forming part of a mechanical stimulation cycle. Alternatively a stationary drive carriage could be employed, for example having opposed rotatable wheels between which the needle is positioned, such that the needle may be driven to and fro.

When the needle is moved in accordance with the drive carriage, each predetermined position of the needle will correspond to a respective position of the needle will correspond to a respective position of the drive carriage. In order to prevent the movement of the needle beyond the predetermined position in the event of a fault, the stop may be arranged to physically obstruct the motion of the drive carriage past the respective drive carriage position.

The position selecting element may also be arranged at the respective drive carriage positions and the stop may therefore form part of the position selecting element. The position selecting element will preferably comprise sensors located at or adjacent to two or more drive carriage positions. Preferably the sensors will be arranged to detect the presence of the stop, the position of the stop being used not only to obstruct the drive carriage but to select the predetermined needle position.

A pin serves as a suitable stop and the drive carriage positions may be equipped with corresponding pin retaining elements.

The presence of the pin within the pin retaining element may be detected using a Hall effect sensor when the pin has a corresponding magnetic portion.

In addition, the IMS device may further comprise a sensor to detect when the device is correctly located in order to perform an IMS cycle. This may be achieved in connection with an applicator unit where a limited range of movement is provided in the first direction for the applicator unit and a biasing member is also provided to bias the applicator unit towards the front of the device and against the subject's body. The biasing element will preferably be arranged such that in use, the force of the applicator unit against the body of the patient will overcome the biasing effect such that the applicator unit is moved towards the other end of its range along the first direction.

A reduction in the pressure will therefore cause the movement of the unit towards the body of the patient and this movement may be detected by a sensor arranged to produce a signal to terminate any IMS cycle being performed. An adjustable member may also be provided to adjust the force of this bias.

The movement of the drive carriage will typically be powered by an electric motor and the drive carriage may be arranged to cooperate with a rotating screw member or alternatively a rack and pinion system. In general, the control of the motor will be provided by a microprocessor in communication with the various sensors of the device.

Conventional automatic IMS devices are operated using a foot pedal system in which a depression of the foot pedal when the gun is in the correct position causes a treatment cycle to be initiated. The needle is inserted into the subject and the stimulation is performed followed by the withdrawal of the needle. However, although this proves to be less tiring than the corresponding manual method, the physician may still be susceptible to repetitive strain injury and fatigue as the number of patients treated in one day can be increased.

In accordance with a third aspect of the present invention, we provide a method of controlling an intramuscular stimulation device, the method comprising the steps of:
  i) causing the device during an operating time period to take up an active condition in which it can perform an intramuscular stimulation operation; and,
  ii) during the operating time period repeatedly determining if a predetermined condition exists for performing an intramuscular stimulation operation and if it does, performing the intramuscular stimulation operation and extending the operating time period.

The method according to this aspect of the present invention therefore reduces the risk of repetitive strain injury and fatigue for the operator of the IMS device. A confirmation signal indicating the existence of the predetermined condition, may be provided by a suitable sensor. In this way, repeated depression of a foot plate or the repeated squeezing of a trigger is avoided. The safety of the system is assured by allowing an IMS operation to be performed only during the time period.

Preferably the step of repeatedly determining if a predetermined condition exists will be performed during the intramuscular stimulation operation in addition to at other times during the operation time period. If during an IMS operation it is determined that the condition is not satisfied then the IMS operation will be terminated and the needle withdrawn.

Typically the predetermined condition will be an indication that the device is correctly positioned against the body of a subject in order to perform an IMS operation.

This may be achieved with a suitable sensor to detect for example when the intramuscular stimulation device is positioned either adjacent to or in contact with the body of a subject.

The method may be arranged such that the IMS operation may be repeatedly performed at one location by reapplying the applicator to the patient. During such a time the predetermined condition allowing the operation of the device may therefore be continually satisfied. However, preferably the method further comprises preventing the performance of a further IMS cycle unless it is determined that the predetermined condition does not exist at a time following the previous IMS cycle. In this way only a single IMS operation can be performed during a period when the predetermined condition is satisfied.

To further enhance safety, the method may further comprise issuing an audible warning prior to each operation of the device.

In accordance with a fourth aspect of the present invention, we provide an intramuscular stimulation unit comprising:

an intramuscular stimulation device to which a needle is attached in use for performing intramuscular stimulation; and a processor for operating the intramuscular stimulation device according to the method of the third aspect of the present invention.

Such an intramuscular stimulation unit may form part of the system for use in conjunction with a disposable needle applicator unit according to the first aspect of the present invention. In this case the intramuscular stimulation unit may be arranged in accordance with the second aspect of the present invention.

BRIEF DESCRIPTION OF THE DRAWINGS

Some examples of an intramuscular stimulation apparatus and method will now be described with reference to the accompanying drawings, in which:

FIG. 5 is an overview of an IMS treatment cycle according to the first example.

DETAILED DESCRIPTION OF THE PREFERRED EMBODIMENTS

Figure 1:
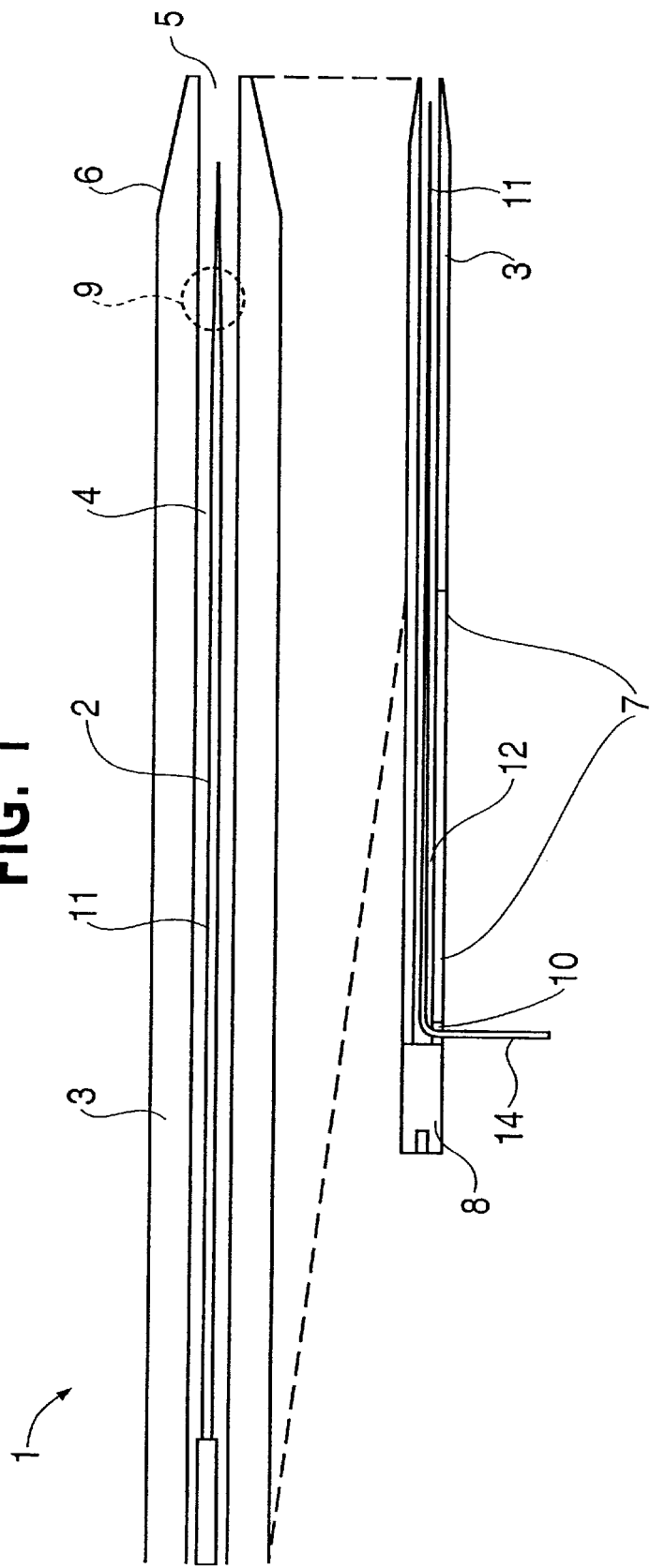
FIG. 1 is an illustration of a disposable needle applicator unit according to a first example.

A disposable needle applicator unit for use in association with a corresponding gun is generally shown at 1 in FIG. 1. The applicator unit has a needle 2 positioned within a sheath 3, the sheath having an internal bore 4 terminating in an end opening 5 at a front end 6 of the sheath, the front end being externally tapered. The bore 4 has a square cross-section for ease of moulding during manufacture.

An elongate slot 7 forms a second opening to the bore 4, the slot being positioned with the sheath rearward with respect to the front end 6. The bore 4 terminates substantially parallel to the rear most part of the slot 7.

The rear end of the sheath is provided by a block 8 for contacting a corresponding component of the gun.

Two projections 9 are disposed upon opposite sides of the sheath adjacent the tapering portion of the front end 6 to allow the applicator unit to be coupled to the gun.

The sheath also contains a detent 10 arranged adjacent the rear most portion of the slot in order to hold the needle in the sheath when not attached to the gun.

The needle 2 of the present example comprises two coupled components 11 and 12, the component 11 being a stimulation portion of the needle 2 for insertion into the body of a patient, the component 12 being a support portion for coupling the stimulation portion to the drive mechanism of the gun.

The stimulation portion 11 has a similar profile to a standard monopolar EMG needle electrode used for electromyographic recording. It is constructed from a conventional metallic alloy for use in the body such as stainless steel and is coated in a friction reducing layer of PTFE. The stimulation and support portions 11, 12 are each elongate in structure although the support portion contains a bore along its length into which the rearward end of the stimulation portion is fully inserted.

The frontmost 1 mm of the stimulation portion of the needle has a tip sharpened such that the PTFE layer is removed allowing direct contact between the metal of the tip and the patient's tissue.

The end of the support portion containing the rear end of the stimulation portion is turned through approximately 90° to form a coupling end 14 of the needle and to secure the stimulation portion.

The sheath 3 comprises two plastic mouldings assembled by means of integral mating pegs and holes, and retained by heating staking. The needle is located by inserting it through the slot in the sheath and pulling it back so that it clicks into the detent such that the needle will not project from the front end opening 5 until connected to the IMS gun.

The coupling end of the needle 14 projects from the slot 7 and, once the detent 10 is deflected, the needle may move along the bore as defined by the full range of motion possible for the coupling end 14 within the slot 7.

When the coupling end 14 is at the rearmost portion of the slot, the tip of the needle will be contained within the sheath and lie a few millimeters from the opening 5 of the sheath. Conversely, when the coupling end 14 is at the frontmost position within the slot 7, an approximate 75 mm length of the stimulation portion will project from the opening 5 of the sheath. This represents the maximum selectable insertion depth.

Following production, the applicator unit containing the needle would then be sealed into a pouch and sterilized typically by the use of ethylene oxide gas.

Figure 2:
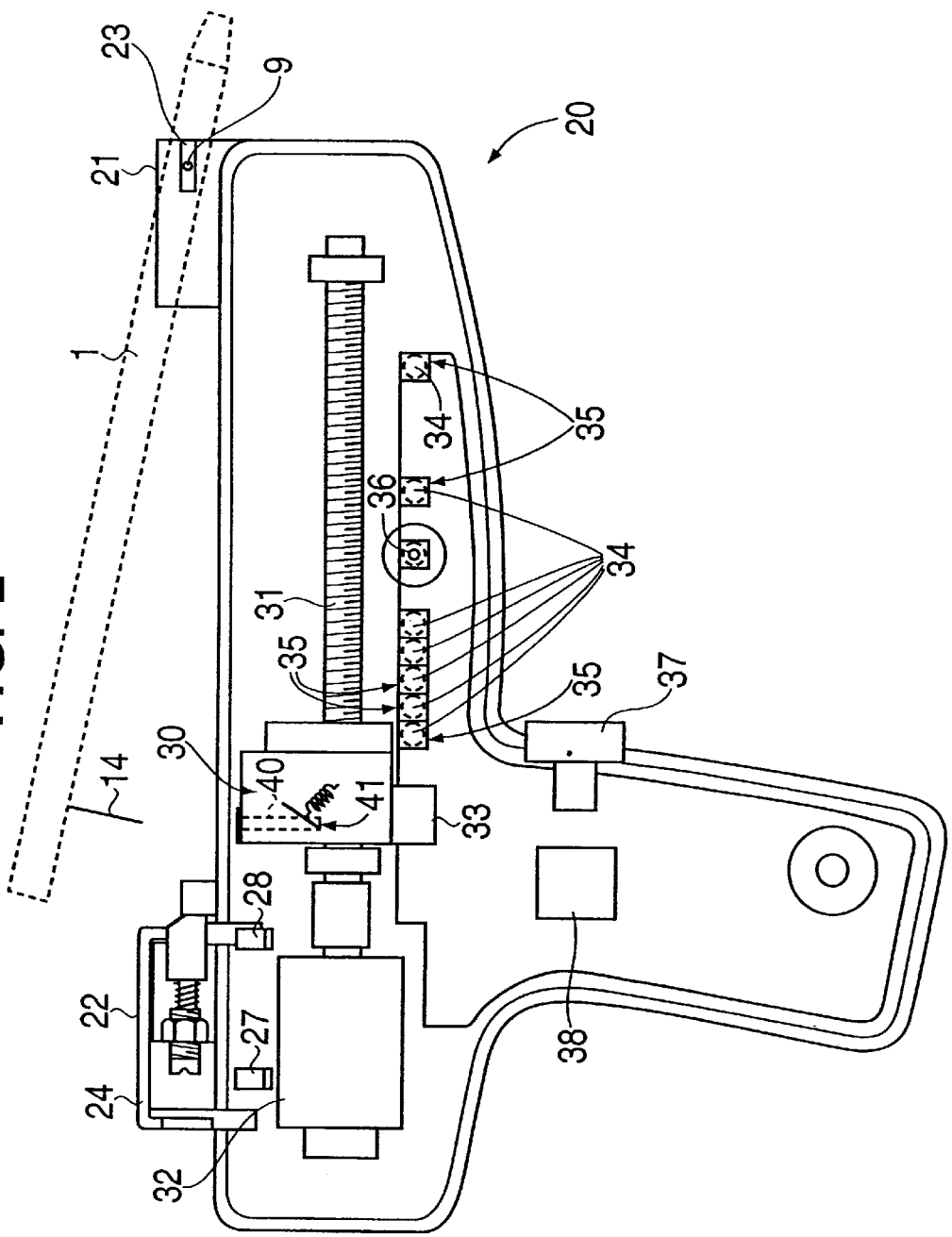
FIG. 2 illustrates a gun according to the first example to which the disposable needle applicator unit is attached in use.

FIG. 2 shows an IMS gun 20. The gun has a front mount 21 positioned in a forward location on top of the gun and a rear mount 22 in a corresponding location at the rear of the gun. The front mount 21 is divided into two components positioned upon each side of the top of the gun 20. In use, the applicator unit is positioned between the two components, each of which has a front facing slot 23. The projections 9 of the applicator unit are inserted into the slots 23.

As shown in FIG. 2, the applicator unit may then be pivoted about the mounted projections 9 such that it may be placed substantially parallel to the top of the gun 20, with the coupling end 14 of the needle projecting downwards into the gun and coupling with a drive mechanism to be described below.

Figure 3:
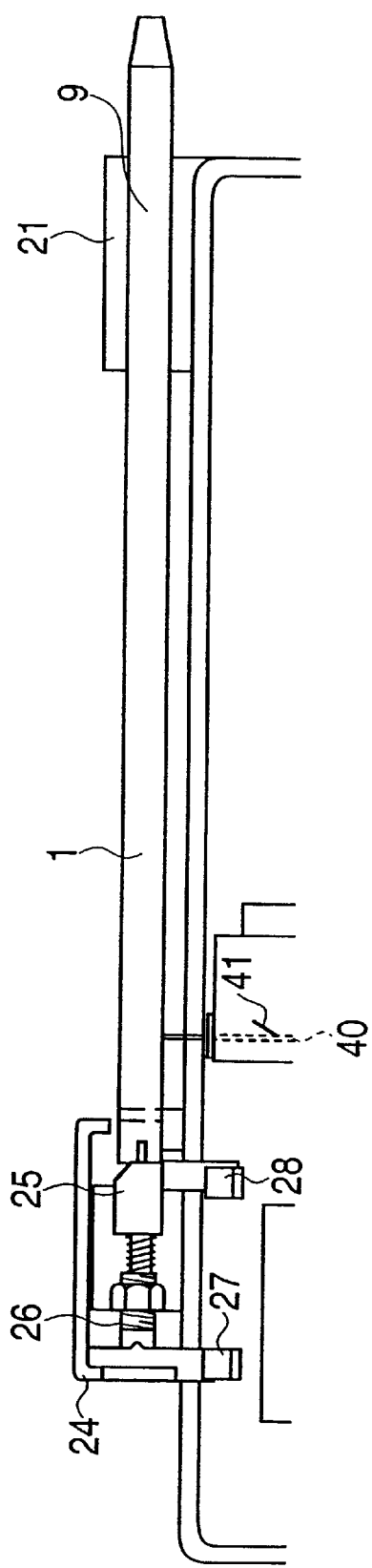
FIG. 3 shows the needle applicator unit when attached to the gun of the first example.

The rear mount 22 has a slidable cover 24 which, when the applicator unit is correctly located horizontally on top of the gun, is slid forward to cover the rear end of the sheath. This is shown more clearly in FIG. 3. FIG. 3 also shows a plunger 25 positioned to contact the rear block 8 of the applicator unit, the plunger being biased in a direction towards the front of the gun. The plunger 25 has a ramped front surface so that as the applicator unit is pushed down, the plunger is forced back against the bias.

The plunger is biased by an adjustable bias mechanism 26 including a spring which applies a predetermined force to the plunger and pushes the applicator unit in a direction towards the front of the gun. The slots 23 of the front mount 21 and the plunger 25 allow some limited movement of the applicator unit in a direction parallel to the top of the gun and the elongate axis of the applicator unit.

An optical detector shown at 27 in FIGS. 2 and 3, is positioned to provide a signal when the slidable cover 24 is in its position covering the rear of the applicator unit. A second optical sensor 28 is positioned to detect movement of the applicator unit in a horizontal direction along the gun. This is used to initiate a stimulation cycle by the gun when the applicator unit moves rearward due to contact with the patient's skin.

Returning to FIG. 2, the gun 20 contains a drive carriage 30 which is movable along a rotatable lead screw 31. The lead screw 31 extends in a direction substantially parallel to that of the top of the gun and therefore also substantially parallel to the elongate direction of the applicator unit when loaded correctly for an IMS treatment cycle.

The lead screw is driven by a motor 32 arranged in the rear of the gun. The motor is equipped with a digital encoder so as to allow accurate monitoring of the motor position during use. In use, the motor rotates the lead screw 31 and the carriage 30 is moved to and fro along the direction of the screw. Power for the motor and the gun systems is provided by a separate low voltage power supply.

In the present example, the coupling end 14 of the needle is pushed into a corresponding drive socket 40 arranged in the drive carriage 30. The drive carriage 30 is located in a default starting location suitable for coupling with the needle. Within the drive socket 40 a biased contact 41 engages with the needle so as to allow the passage of electrical current through the needle and into the patient. The needle is released from behind the detent 10 by causing the detent 10 to deflect.

A blade 33 is positioned beneath the drive carriage 30 and a number of Hall effect sensors 34 are arranged in a row parallel to the lead screw 31 at predetermined positions along its length. The Hall effect sensors 34 are located such that the blade passes adjacent to them when the drive carriage 30 is moved along the lead screw 31.

The location of the Hall effect sensors corresponds to a number of positions of the drive carriage which in turn correspond to each of the predetermined needle positions. These positions correspond to various penetration depths of the needle into the body of the patient.

At the location of each Hall effect sensor, a pin retaining element 35 is arranged such that a pin 36 may be inserted through corresponding openings (not shown) in the housing of the gun 20 such that the long axis of the pin lies transverse to the direction of motion of the drive carriage.

In use, a single pin is positioned within one of the openings and is held within the respective pin retaining element 35. The pin retaining elements 35 are arranged such that when a pin is inserted into one of the elements, the end of the pin lies adjacent or in contact with the Hall effect sensor surface.

The openings and pin retaining elements 35 are also arranged such that the blade 33 will impact upon the pin when the pin is located in the pin retaining element. In general, the entire pin may be manufactured from a magnetizable material or will contain a magnet sufficiently powerful to operate the relevant Hall effect sensor.

When a pin is inserted within the pin retaining element 35, the relevant Hall effect sensor outputs a signal which indicates that presence of the pin. This signal is interpreted by a processor to indicate the desired depth for the penetration of the needle and therefore acts as a depth selection device.

The pin 36 therefore has a dual purpose in that, on the one hand it provides a detectable effect upon the relevant Hall effect sensor which informs the gun 20 of the selected position, and on the other provides a physical obstruction to the passage of the blade 33 if it attempts to pass beyond the selected position, due for example to a fault in the control system.

A processor 38 is provided in order to control the movement of the drive carriage 30 using the motor 32. This is achieved in response to the information received from the sensors 27, 28 and 34. In addition, a trigger 39 is provided which acts as a switch to initiate an arming cycle to be described below.

A number of control buttons and a display are also provided (not shown) on the housing of the gun. These are used to enable the physician to select the stimulation mode required along with other associated parameters. The display may also be used to provide information such as the number of cycles performed and the reason for any termination of an IMS cycle.

The operation of the gun and disposable needle applicator unit in performing an IMS treatment cycle will now be described with reference to FIGS. 4 and 5.

Figure 4:
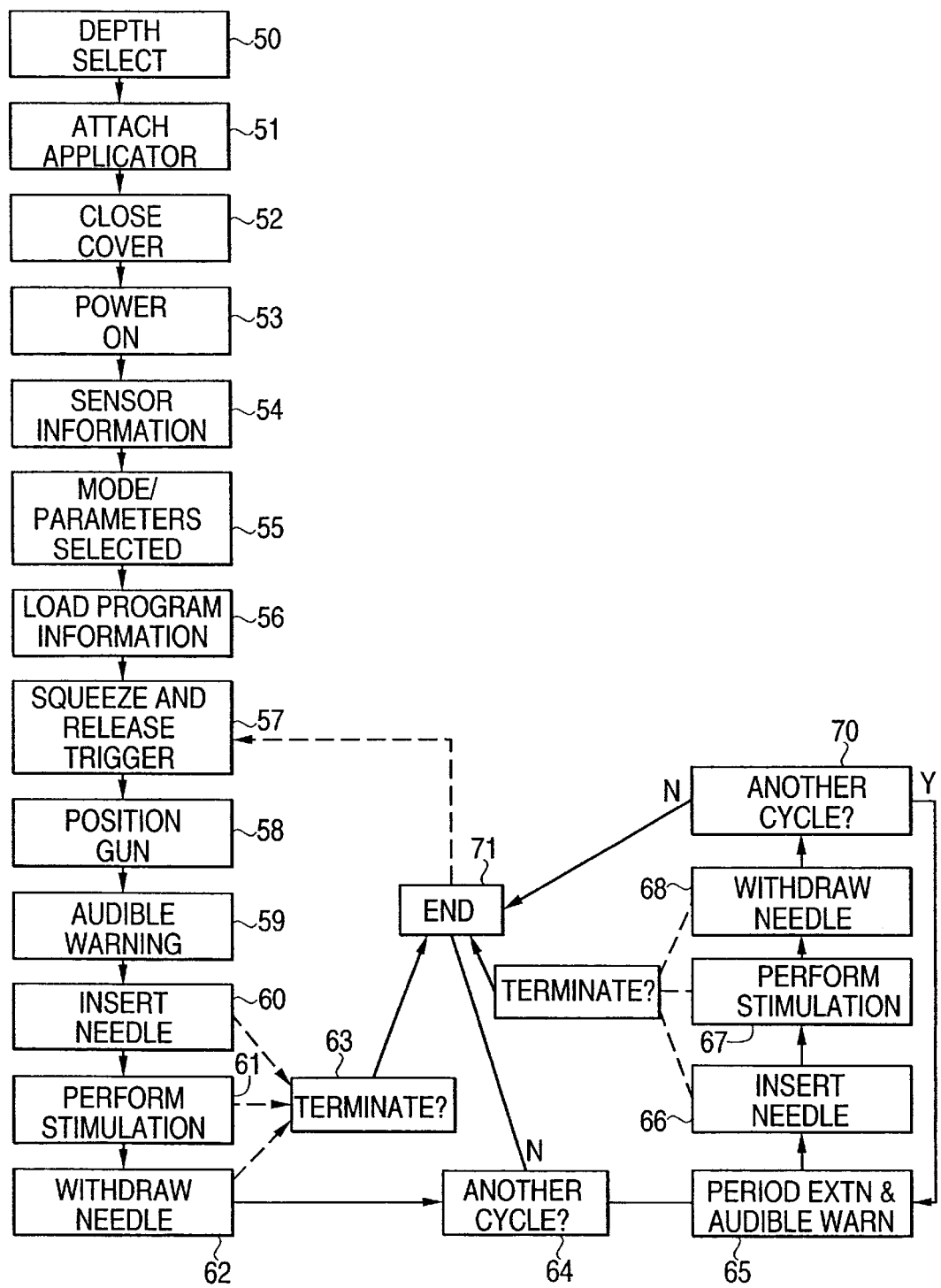
FIG. 4 is a flow diagram illustrating the operation of the gun and needle applicator unit according to the first example.

FIG. 4 shows a flow diagram of the operation of the gun during a typical IMS treatment cycle.

The physician firstly positions the patient conveniently to provide access to the muscles for treatment. At step 50 the physician selects a penetration depth by inserting the pin 36 through one of the openings into a pin retaining element 35.

At step 51, the physician removes the needle applicator unit from a sealed sterile container and positions the front end of the applicator unit between the front mount components 21 of the gun 20. The applicator unit is attached to the front of the gun by moving the applicator unit in a rearward direction so as to hook the projections 9 into the corresponding slots 23 in the front mount of the gun.

The physician then pivots the applicator unit about the projections 9 so as to insert the coupling end 14 of the needle into the corresponding drive socket 40 of the drive carriage 30.

Pushing down upon the rear end block 8 of the applicator unit also displaces the plunger 25 rearward due to the ramp upon its face, and the adjustable bias 26 ensures that the applicator unit is urged into its most forward position.

Some adjustment of the adjustable bias may be made according to the physician's judgement as to the ease with which the sheath should be allowed to move with respect to the IMS gun.

The slidable cover 24 is then slid into place at step 52 and the gun is turned on at step 53. This causes the processor 38 at step 54 to determine whether the optical detector 27 is indicating that the slidable cover 24 is shut and therefore that the applicator unit is correctly secured. In addition, at step 54 the processor 38 determines which depth has been selected by the physician by examining signals from the sensors 34.

The physician selects the operation mode and associated parameters at step 55 using the buttons and display mounted to the handle of the gun.

In the present example the available modes are a mechanical mode, an electrical mode, or a combination of mechanical and electrical stimulation. There are also associated settings for each mode such as the range of mechanical reciprocation of the needle, its frequency and the pulse amplitude and pulse frequency applied during electrical stimulation.

Steps 50 to 55 may be carried out in any order and, after selection of the mode and parameters, at step 56, the processor 38 loads the corresponding cycle program information from a store (not shown) containing a look-up table. This information includes data such as the sequence and number of turns to be applied to the motor, the operation of which is closely monitored using feedback from the encoder.

The trigger 39 is then squeezed and released by the physician which initiates an arming cycle (step 57).

The physician then places the tapered front end 6 of the applicator unit against the skin of the patient at step 58. The action of pushing the applicator unit against the skin overcomes the biasing force of the adjustable bias 26 and the applicator unit is forced rearward such that the projections 9 impact against the end of the front facing slots 23.

The optical detector 28 senses the movement of the applicator unit to this position and emits a signal 82 as long as the applicator unit is so positioned.

Referring to FIG. 5, when the processor determines that the trigger has been squeezed (step 57) via a signal 80, a 15 second arming cycle 81 is initiated. If during this 15 seconds the processor detects the signal 82 from the detector 28 indicating that the applicator unit is pressed against the skin, a one second audible warning 83 is issued (step 59).

The processor 38 then activates the motor 32 (step 60) to rapidly insert the needle to the predefined depth in accordance with the selected position of the pin 6. The position of the drive carriage is constantly tracked by the processor 38 using information received from the motor encoder. When the needle is positioned at the predefined depth the blade 33 is located adjacent to the pin 6.

Should any malfunction of the device occur, the pin will physically prevent the motion of the blade and the drive carriage 30 further along the gun.

When the drive carriage is correctly positioned and the needle inserted to the desired depth, one of three stimulation modes selected at step 53 is then performed at step 61. This is also shown at 84 in FIG. 5.

A typical mechanical stimulation operation involves the repeated reciprocation of the needle through a stroke length of a few millimeters at a frequency of around two cycles per second. The stroke is arranged such that the maximum depth of the needle corresponds to the depth of the predetermined needle position from which the reciprocating motion begins. The reciprocating motion may be continued for a number of seconds (shown at 85 in FIG. 5) followed by the complete withdrawal of the needle at step 62 (also shown at 86 in FIG. 5).

An electrical stimulation cycle may be performed at steps 61 and 67 either in place of or in conjunction with a manual stimulation cycle. In this case, the processor controls the delivery of electrical stimuli having predetermined parameters such as current, voltage and frequency through the needle to the motor point within the patient's body. This is achieved through the biased contact 41 which electrically connects the drive carriage 30 to the needle coupling end 40. In this mode a second electrode will be attached to the patient's skin in order to complete the electrical circuit.

As shown in FIG. 5 the contact of the applicator unit with the skin is indicated by the signal 82 which remains at a high level throughout any contact period. The transition from the low level to the high level of this signal causes the initiation warning 83 to be emitted audibly followed by the performance of the IMS cycle.

Throughout the intramuscular stimulation cycle at steps 59 to 61, the status of the signal 82 is constantly monitored by the processor 38. If the applicator unit for any reason moves towards the front of the gun due to insufficient force being applied by the physician, deliberate withdrawal of the applicator unit contact or recoil due to the needle striking an obstruction such as bone, the signal 82 will drop to a low level and the cycle will be terminated at step 63 by immediate withdrawal of the needle 2.

During normal operation, following the withdrawal of the needle, the physician removes the gun and this causes the applicator unit to be forced forward by the adjustable bias 26 and the signal 82 from the optical detector 28 then falls to a low level.

The physician may then select a second location in which to perform a second IMS treatment cycle during the remainder of the time period 81. The processor 38 monitors for further contact of the applicator unit with the body of the patient at step 64. If another contact 88 is detected at step 64 within the period 81 then a second intramuscular stimulation cycle will be initiated and it should be noted that this occurs without the physician squeezing the trigger 39. The time period is then extended at step 65 for example by a further 15 seconds as shown at 87 and another one second audible warning 89 is issued.

Another treatment cycle 90,91,92 is performed at steps 66 to 68 which are identical to steps 60 to 62. Throughout the treatment cycle at step 69, the signal 82 is monitored in an identical manner to step 63 for a transition between the high level and the low level. If a transition in the signal 82 is detected then the cycle is immediately terminated.

At step 70 if the end of the extended period is reached without a further rise to the high level of the signal 82, then the arming cycle 81 is terminated at step 71. This of course may also occur at step 64 after the first treatment cycle. No further operation of the gun is then possible unless the physician squeezes the trigger 39 to begin the process again at step 57.

It will be appreciated that steps 65 to 70 may be repeated indefinitely as long as transition from the low to the high level of the signal 82 is detected within each extended time period.

This allows the physician to perform a number of consecutive stimulation cycles requiring only the trigger to be squeezed and released once.

Once the treatment has been completed by the physician the arming cycle 81 simply terminates at the end of the respective period. Sliding back the cover 24 then disables the gun completely.

The applicator unit may then be detached for disposal, the action of detachment causing the detent 10 to hold the needle safely in the retracted position.

What is claimed is:

1. A disposable needle applicator unit for attachment to an intramuscular stimulation device, the applicator unit comprising:
    a needle having an elongate first end portion for insertion into the body of a subject and a second end portion for coupling with a drive carriage of the intramuscular stimulation device; and,
    an elongate sheath for enclosing at least the first end portion of the needle, the sheath having a first opening in one end from which the first end portion of the needle may be extended, and a second opening allowing the second end portion of the needle to be coupled with the drive carriage, wherein the second opening of the sheath is a slot arranged in the side of the sheath.

2. An applicator unit according to claim 1, wherein the second end portion of the needle projects through the second opening of the sheath so as to couple with the drive carriage in use.

3. An applicator unit according to claim 1, wherein the first end portion of the needle is coated with a friction reducing layer.

4. An applicator unit according to claim 1, further comprising an attachment element for attaching the unit to the intramuscular stimulation device.

5. An applicator unit according to claim 4, wherein the attachment element comprises one or more projections extending from a forward portion of said sheath for coupling with one or more corresponding elements on the intramuscular stimulation device.

6. An applicator unit according to claim 1, further comprising a contact block arranged at the rear of the sheath with respect to the first opening, wherein in use, the contact block couples with a corresponding component of the intramuscular stimulation device, such that the applicator unit is attached to the intramuscular stimulation device.

7. A disposable needle applicator unit for attachment to an intramuscular stimulation device, the applicator unit comprising:
    a needle having an elongate first end portion for insertion into the body of a subject and a second end portion for coupling with a drive carriage of the intramuscular stimulation device; and,
    an elongate sheath for enclosing at least the first end portion of the needle, the sheath having a first opening in one end from which the first end portion of the needle may be extended, and a second opening allowing the second end portion of the needle to be coupled with the drive carriage, said applicator unit further comprising a detent arranged to releasably retain the needle such that the first end portion of the needle is enclosed within the sheath when the applicator unit is not attached to the intramuscular stimulation device.

8. An intramuscular stimulation system comprising:
    a disposable needle applicator unit according to claim 1; and
    an intramuscular stimulation device to which the disposable needle applicator unit is attached in use, for performing intramuscular stimulation of a subject.

9. An intramuscular stimulation system according to claim 8, wherein the second end portion of the needle projects through the second opening of the sheath so as to couple with the drive carriage in use.

10. An intramuscular stimulation system according to claim 8, wherein the first end portion of the needle is coated with a friction reducing layer.

11. An intramuscular stimulation system according to claim 8, further comprising an attachment element for attaching the unit to the intramuscular stimulation device.

12. An intramuscular stimulation system according to claim 11, wherein the attachment element comprises one or more projections extending from a forward portion of said sheath for coupling with one or more corresponding elements on the intramuscular stimulation device.

13. An intramuscular stimulation system according to claim 8, further comprising a contact block arranged at the rear of the sheath with respect to the first opening, wherein in use, the contact block couples with a corresponding component of the intramuscular stimulation device, such that the applicator unit is attached to the intramuscular stimulation device.

14. An intramuscular stimulation system comprising:
    a disposable needle applicator unit for attachment to an intramuscular stimulation device, the applicator unit comprising:
        a needle having an elongate first end portion for insertion into the body of a subject and a second end portion for coupling with a drive carriage of the intramuscular stimulation device; and,
        an elongate sheath for enclosing at least the first end portion of the needle, the sheath having a first opening in one end from which the first end portion of the needle may be extended, and a second opening allowing the second end portion of the needle to be coupled with the drive carriage; and
    an intramuscular stimulation device to which the disposable needle applicator unit is attached in use, for performing intramuscular stimulation of a subject;
    said system further comprising a detent arranged to releasably retain the needle such that the first end portion of the needle is enclosed within the sheath when the applicator unit is not attached to the intramuscular stimulation device.

15. An intramuscular stimulation device comprising:
    a drive carriage to which a needle is coupled in use, the drive carriage being arranged so as to move the needle in a first direction to one of a number of predetermined positions for subsequently performing intramuscular stimulation of a subject;
    a drive motor arranged to operate the drive carriage;
    a position selecting element arrange to produce a signal identifying the selection of a particular predetermined position from the number of predetermined positions, the signal being used in accordance with the drive motor and drive carriage to move the needle in the first direction to the selected predetermined position; and,
    a stop which can be located in accordance with the selected predetermined position so as to prevent the needle from moving past the selected predetermined position.

16. A device according to claim 15, wherein the drive carriage has a hole into which a portion of the needle is coupled during use.

17. A device according to claim 15, wherein drive carriage is arranged to be driven to and fro in the first direction.

18. A device according to claim 17, wherein each predetermined position of the needle has a corresponding drive carriage position and wherein the stop is arranged to prevent the motion of the drive carriage past the drive carriage position corresponding to the selected predetermined position of the needle.

19. A device according to claim 18, wherein the stop is positioned at or adjacent the drive carriage positions and wherein the position selecting element has sensors located at or adjacent to two or more drive carriage positions, the sensors being arranged to detect the presence of the stop.

20. A device according to claim 18, wherein the stop is a pin and wherein the drive carriage positions have pin retaining elements such that when the pin is positioned within a pin retaining element the movement of the drive carriage past the drive carriage position is prevented by contact of the drive carriage with the pin.

21. A device according to claim 19, wherein the sensor is a Hall Effect sensor and wherein the stop is magnetic.

22. A device according to claim 19, wherein the stop is a pin and wherein the drive carriage positions have pin retaining elements such that when the pin is positioned within a pin retaining element the movement of the drive carriage past the drive carriage position is prevented by contact of the drive carriage with the pin.

23. A method of operation carried out by an intramuscular stimulation device, the method comprising the steps of:

(i) taking up, during an operating time period, an active condition in which the device can perform an intramuscular stimulation operation; and, (ii) during the operating time period repeatedly determining if a predetermined condition exists for performing an intramuscular stimulation operation and if it does, performing the intramuscular stimulation operation and extending the operating time period, wherein the predetermined condition comprises an indication that the device is correctly positioned against the body of a subject.

24. A method according to claim 23, wherein the step of repeatedly determining if a predetermined condition exists is performed during the intramuscular stimulation operation and wherein the intramuscular stimulation operation is terminated if the predetermined condition is determined not to exist during the intramuscular stimulation operation.

25. A method according to claim 23, wherein the method further comprises, preventing the performance of a further intramuscular stimulation cycle unless it is determined that the predetermined condition does not exist at a time following the previous intramuscular stimulation cycle.

26. A method according to claim 23, further comprising issuing an audible warning prior to each intramuscular stimulation.

27. A method according to claim 24, wherein the method further comprises preventing the performance of a further intramuscular stimulation cycle unless it is determined that the predetermined condition does not exist at a time following the previous intramuscular stimulation cycle.

28. A method according to claim 23, wherein the predetermined condition comprises an indication that the device is correctly positioned against the body of the subject, following an indication that the device is not positioned against the body of the subject, both indications occurring during the operating time period.

29. An intramuscular stimulation unit comprising:

an intramuscular stimulation device to which a needle is attached in use for performing intramuscular stimulation; and a processor for operating the intramuscular stimulation device such that:

i) the device is, during an operating time period, caused to take up an active condition in which it can perform an intramuscular stimulation operation; and ii) during the operating time period it is repeatedly determined if a predetermined condition exists for performing an intramuscular stimulation operation and if it does, performing the intramuscular stimulation operation and extending the operating time period, wherein the predetermined condition comprises an indication that the device is correctly positioned against the body of a subject.

30. An intramuscular stimulation unit according to claim 29, wherein the step of repeatedly determining if a predetermined condition exists is performed during the intramuscular stimulation operation and wherein the intramuscular stimulation operation is terminated if the predetermined condition is determined not to exist during the intramuscular stimulation operation.

31. An intramuscular stimulation unit according to claim 29, wherein the intramuscular stimulation device operates such than an audible warning is issued prior to each intramuscular stimulation operation.

32. An intramuscular stimulation unit according to claim 29, wherein the processor operates the intramuscular stimulation device such that the performance of a further intramuscular stimulation cycle is prevented unless it is determined that the predetermined condition does not exist at a time following the previous intramuscular stimulation cycle.

33. An intramuscular stimulation unit according to claim 29, wherein the predetermined condition comprises an indication that the device is correctly positioned against the body of the subject, following an indication that the device is not positioned against the body of the subject, both indications occurring during the operating time period.

* * * * *